US00PP12422P2

(12) United States Plant Patent
Danziger

(10) Patent No.: US PP12,422 P2
(45) Date of Patent: Feb. 26, 2002

(54) GYPSOPHILA PLANT NAMED 'DANGYPFLASH'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/489,009

(22) Filed: Jan. 21, 2000

(51) Int. Cl.[7] ..... A01H 5/00
(52) U.S. Cl. ..... Plt./354
(58) Field of Search ..... Plt./354

(56) References Cited

PUBLICATIONS

UPOV–ROM GTITM Computer Database 2001/01 Feb. 6, 2001, GTI Jouve Retrieval Software, Citation for 'Dangypflash'.*

Breeder's Rights Certificate Application No. 2966/98 State of Israel.

UPOV Report on Technical Examination Ref. No. 2966 State of Israel.

* cited by examiner

*Primary Examiner*—Bruce R. Campell
*Assistant Examiner*—Annette H. Para
(74) *Attorney, Agent, or Firm*—Foley & Lardner

(57) ABSTRACT

A new and distinct Gypsophilia plant named 'Dangypflash' characterized by having upright, uniform growth habit yielding 8–10 stems per plant; stable, conic-shaped inflorescence; white, large, 10–11 mm, semi-to-full double flower depending on growing conditions; absence of deformation or discoloration; early flowering plant, 8–9 weeks in summer; and year-round growing season under regular cultural practices which makes the new cultivar suitable for both indoor and outdoor cultivation.

1 Drawing Sheet

BACKGROUND OF THE INVENTION

The present invention comprises a new and distinct cultivar of Gypsophila plant, botanically known as *Gypsophila paniculata* and hereinafter referred to by the cultivar name 'Dangypflash'.

The new cultivar 'Dangypflash' was originated from a cross made in a controlled breeding program in Mishmar Hashiva, Israel in 1997. The male parent is a Gypsophila cultivar designated cv. 417, from the breeding program designated as hybrid line "C". The female parent is a Gypsophila cultivar designated cv. 202, from the breeding program designated as hybrid line "D". 'Dangypflash' was discovered and selected by the inventor, Gabriel Danziger, within the progeny of the stated cross in a controlled environment in Mishmar Hashiva, Israel.

Asexual reproduction of the new cultivar was accomplished by the inventor by removing cuttings from the initial plant in a controlled, greenhouse environment at Mishmar Hashiva, Israel in September 1997, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Dangypflash' which in combination distinguish this Gypsophila as a new and distinct cultivar:

1. upright, uniform growth habit yielding 8–10 stems per plant;

2. stable, conic-shaped inflorescence;

3. white, large, 10–11 mm, semi-to-full double flower depending on growing conditions;

4. absence of deformation or discoloration;

5. early flowering plant, 8–9 weeks in the summer; and 6. year-round growing season under regular cultural practices which makes the new cultivar suitable for both indoor and outdoor cultivation.

'Dangypflash' has not been observed under all possible environmental conditions. The phenotype of the new cultivar may vary with variations in environment such as temperature, light intensity and daylength without a change in the genotype of the plant. The following observations, measurements and values describe the new cultivar as grown in Mishmar Hashiva, Israel under conditions which closely approximate those generally used in commercial practice.

Of the many commercial cultivars known to the present inventor, the most similar in comparison to 'Dangypflash' is the cultivar 'Magic Arbel' (U.S. Plant Pat. No. 9,312). In comparison to 'Magic Arbel', 'Dangypflash' has a higher stem yield, more upright growth habit and no discoloration during winter. In comparison to the parental cultivars, the flower of 'Dangypflash' is fuller.

BRIEF DESCRIPTION OF THE DRAWING

The accompanying photographic illustration shows a typical 'Dangypflash' plant following growth under appropriate growing conditions, with colors being as true as possible with illustrations of this type.

DETAILED BOTANICAL DESCRIPTION

The following is a detailed description of the new cultivar based on 3 month old plants, grown in an open field, produced under commercial practice in Israel. Color references are made to The Royal Horticultural Society Colour Chart (R.H.S.), except where general colors of ordinary significance are used.

Origin: Mishmar Hashiva, Israel.

Parentage:

*Male parent.*—cv. 417, hybrid line "C" from breeding program.

*Female parent.*—cv. 202, hybrid line "D" from breeding program.

Classification:

*Botanical.*—Hybrid of *Gypsophila paniculata.*

*Commercial.*—Gypsophila 'Dangypflash'.

Propagation: Vegetatively by cuttings.

Plant:

*Form.*—Upright bush.

*Growth habit.*—Apical dominance with the side shoots positioned at the basal part of the main stem.

*Mature plant size.*—Height 100 cm; perimeter 60 cm.

Foliage:

*Size.*—Length 9–10 cm, Width 1.5 cm.

*Shape.*—Linear.

*Margin.*—Entire.

*Color.*—Upper surface: RHS 137A. Lower surface: RHS 137B.

*Stipules.*—None.

Flowers:

*Natural flowering season.*—Spring, summer and autum.

*Duration of bloom.*—Vase life of harvested branch is 10–14 days; duration of flowering plant is 4–5 weeks.

*Borne.*—In a panicle shape on 8–9 mm pedicels.

*Quantity.*—Approximately 1,500.

*Petals.*—Shape: Lanceolate with emarginate tip. Size: Approximately 10–11 mm. Color: White, RHS 155D. Petal markings: Transparent margin. Number of petals: Approximately 40–50.

*Buds.*—Shape: Obovate. Diameter: 4 mm. Color: White, RHS 155 B.

Reproductive organs:

*Stamens.*—Undeveloped, less than 10 in number; no coloration.

*Filaments.*—Undeveloped, less than 10 in number; no coloration.

*Anthers.*—Undeveloped, less than 10 in number; no coloration.

*Pollen.*—None.

*Pistils.*—2, convex in shape; color is white, RHS 155 B.

Fruit/seed: None observed.

Resistance to disease: Resistant to most pests and diseases under regular growing conditions.

I claim:

1. A new and distinct Gypsophila plant named 'Dangypflash', substantially as illustrated and described herein.

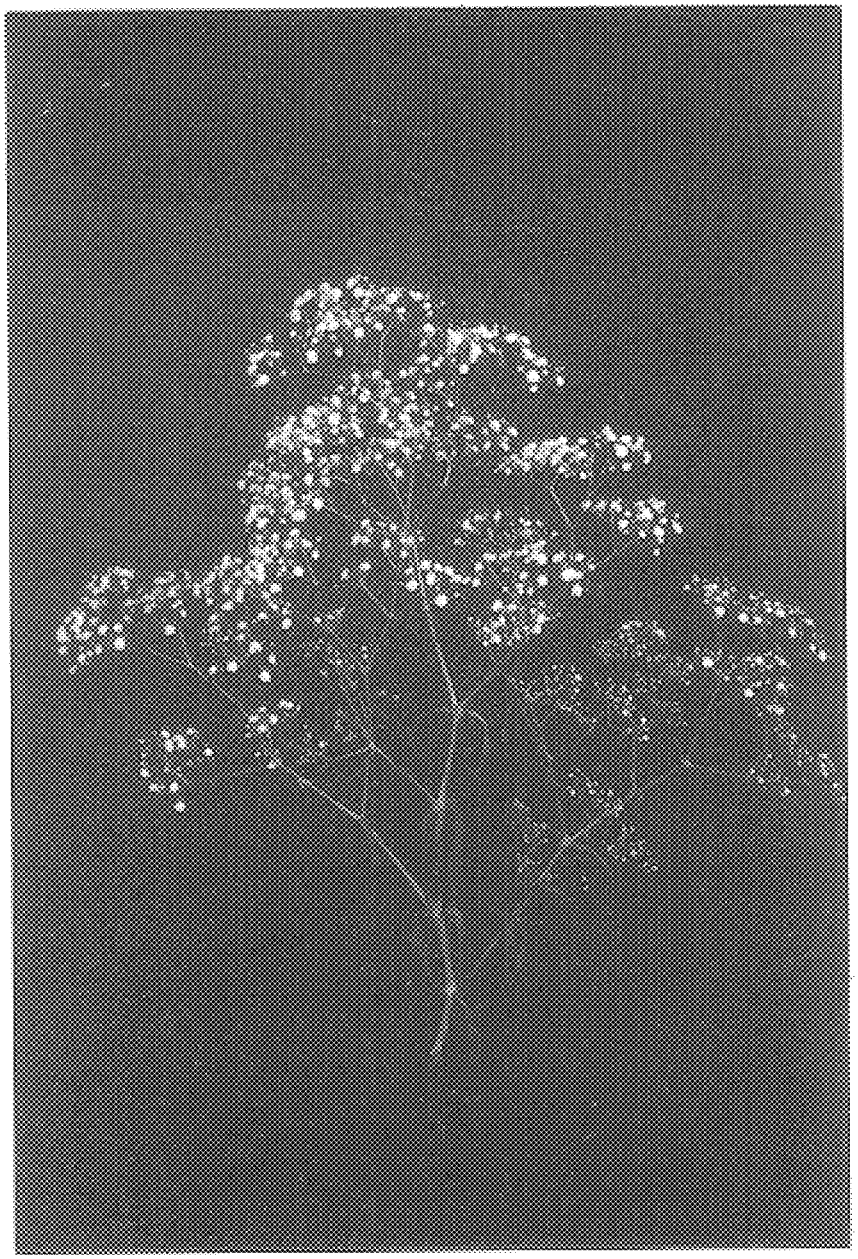

* * * * *